(12) United States Patent
Gupta

(10) Patent No.: US 8,927,592 B2
(45) Date of Patent: Jan. 6, 2015

(54) ANTITUMORAL USE OF CABAZITAXEL

(75) Inventor: Sunil Gupta, Chester Springs, PA (US)

(73) Assignee: Aventis Pharma SA, Antony (FR)

( * ) Notice: Subject to any disclaimer, the term of this patent is extended or adjusted under 35 U.S.C. 154(b) by 0 days.

(21) Appl. No.: 13/456,720

(22) Filed: Apr. 26, 2012

(65) Prior Publication Data
US 2012/0301425 A1 Nov. 29, 2012

Related U.S. Application Data

(63) Continuation of application No. PCT/IB2010/054866, filed on Oct. 27, 2010.

(60) Provisional application No. 61/389,969, filed on Oct. 5, 2010, provisional application No. 61/383,933, filed on Sep. 17, 2010, provisional application No. 61/369,929, filed on Aug. 2, 2010, provisional application No. 61/355,888, filed on Jun. 17, 2010, provisional application No. 61/355,834, filed on Jun. 17, 2010, provisional application No. 61/293,903, filed on Jan. 11, 2010, provisional application No. 61/256,160, filed on Oct. 29, 2009.

(51) Int. Cl.
| | | |
|---|---|---|
| A61K 31/337 | (2006.01) | |
| A61K 31/573 | (2006.01) | |
| A61K 31/164 | (2006.01) | |
| A61K 31/56 | (2006.01) | |
| A61K 45/06 | (2006.01) | |

(52) U.S. Cl.
CPC ............ *A61K 31/337* (2013.01); *A61K 31/164* (2013.01); *A61K 31/56* (2013.01); *A61K 31/573* (2013.01); *A61K 45/06* (2013.01)
USPC ........................................ 514/449

(58) Field of Classification Search
CPC ........................... A61K 31/337; A61K 31/573
See application file for complete search history.

(56) References Cited

U.S. PATENT DOCUMENTS

| | | | |
|---|---|---|---|
| 5,438,072 A | 8/1995 | Bobee et al. | |
| 5,847,170 A | 12/1998 | Bouchard et al. | |
| 5,889,043 A | 3/1999 | Bouchard et al. | |
| 5,962,705 A | 10/1999 | Didier et al. | |
| 6,160,135 A | 12/2000 | Bouchard et al. | |
| 6,331,635 B1 | 12/2001 | Bouchard et al. | |
| 6,346,543 B1 | 2/2002 | Bissery et al. | |
| 6,372,780 B2 | 4/2002 | Bouchard et al. | |
| 6,387,946 B1 | 5/2002 | Bouchard et al. | |
| 6,403,634 B1 | 6/2002 | Bissery | |
| 7,241,907 B2 | 7/2007 | Didier et al. | |
| 7,772,274 B1 | 8/2010 | Palepu | |
| 2002/0038038 A1 | 3/2002 | Bouchard et al. | |
| 2004/0126379 A1 | 7/2004 | Adolf et al. | |
| 2005/0065138 A1* | 3/2005 | Didier et al. .................. | 514/173 |
| 2005/0070496 A1 | 3/2005 | Borovac et al. | |
| 2008/0279923 A1 | 11/2008 | Bradke et al. | |
| 2010/0311825 A1 | 12/2010 | Rortais et al. | |
| 2011/0105598 A1 | 5/2011 | Gurjar et al. | |
| 2011/0144362 A1 | 6/2011 | Billot et al. | |
| 2011/0160159 A1 | 6/2011 | Ryan | |
| 2011/0177970 A1 | 7/2011 | Chauchereau et al. | |
| 2011/0237540 A1 | 9/2011 | Crawford et al. | |
| 2012/0077845 A1 | 3/2012 | Dalton et al. | |
| 2012/0115806 A1 | 5/2012 | Magherini | |

FOREIGN PATENT DOCUMENTS

| | | |
|---|---|---|
| EP | 0817779 | 1/2000 |
| EP | 2177630 | 4/2010 |
| FR | 2732340 | 10/1996 |
| WO | WO 94/18164 | 8/1994 |
| WO | WO 96/30355 | 10/1996 |
| WO | WO 96/30356 | 10/1996 |
| WO | WO 00/10547 | 3/2000 |
| WO | WO 2005/028462 | 3/2005 |
| WO | WO 2006/062811 | 6/2006 |
| WO | WO 2010/117668 | 10/2010 |
| WO | WO 2010/128258 | 11/2010 |
| WO | WO 2011/051894 | 5/2011 |
| WO | WO 2011/063421 | 5/2011 |
| WO | WO 2011/124669 | 10/2011 |
| WO | WO 2011/130317 | 10/2011 |
| WO | WO 2011/130566 | 10/2011 |

OTHER PUBLICATIONS

Mita et al. Clinical Cancer Research, 2009, vol. 15, pp. 723-730.*
Tannock et al. N. Engl. J. Med., 2004, vol. 351, pp. 1502-1512.*
Beardsley et al. Current Opinions in Supportive and Palliative Care, Sep. 2008, vol. 2, pp. 161-166.*

(Continued)

*Primary Examiner* — James D Anderson
(74) *Attorney, Agent, or Firm* — Kelly L. Bender

(57) ABSTRACT

The invention relates to a compound of formula:

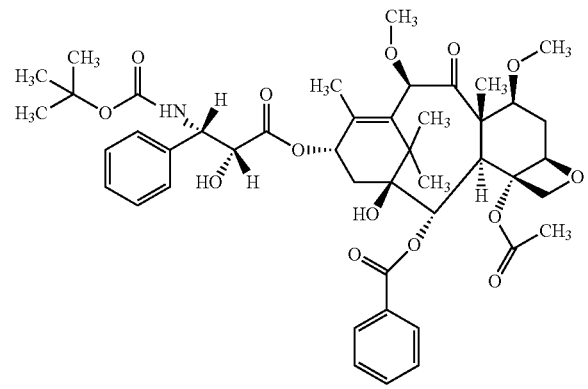

which may be in base form or in the form of a hydrate or a solvate, in combination with prednisone or prednisolone, for its use as a medicament in the treatment of prostate cancer, particularly metastatic prostate cancer, especially for patients who are not catered for by a taxane-based treatment.

30 Claims, 7 Drawing Sheets

(56) References Cited

OTHER PUBLICATIONS

Parkin, et al., Global Cancer Statistics, (2002), CA Cancer J. Clin., (2005), vol. 55, pp. 74-108.
Hellerstedt, et al., The Current State of Hormonal Therapy for Prostate Cancer, CA Cancer J. Clin.,(2002), vol. 52, pp. 154-179.
Horwitz et al., External Beam Radiation Therapy for Prostate Cancer, CA Cancer J. Clin., (2000); vol. 50, pp. 349-375.
Pienta et al., Advances in Prostate Cancer Chemotherapy: A New Era Begins, CA Cancer J. Clin, (2005), vol. 55, pp. 300-318.
Cabral, Factors Determining Cellular Mechanisms of Resistance to Antimitotic Drugs, Drug Resistance Updates, (2001), vol. 4 No. 1, pp. 3-8.
Dumontet, et al., Mechanisms of Action of and Resistance to Antitubulin Agents: Microtubule Dynamics, Drug Transport and Cell Death, J. Clin. Onc., (1999), vol. 17, No. 3, pp. 1061-1070.
Haleblian, et al., Characterization of Habits and Crystalline Modification of Solids and Their Pharmaceutical Applications, J. Pharm. Sci., (1975), pp. 1269-1288.
Melzack, The McGill Pain Questionnaire: Major Properties and Scoring Methods; Pain, vol. 1, (1975), pp. 277-299.
Berry, et al., Quality of Life and Pain in Advanced Stage Prostate Cancer: Results of a Southwest Oncology Group Randomized Trial Comparing Docetaxel and Estramustine to Mitoxantrone and Prednisone, Journal of Clinical Oncology, (2006), vol. 24, No. 18, pp. 2828-2835.
Fizaz, et al., New agents in Metastatic Prostate Cancer, Eur. J. Cancer. 2009, vol. 45, Supp. 1., pp. 379-380.
http://clinicaltrials.gov/archive/NCT0417079/2006_12_28, View of NCT00417079 on Dec. 28, 2006—XRP6258 Plus Predinisone Compared to Miitoxantrone Plus Predisone in Hormaone Refractory Metastatic Prostate Cancer (TROPIC). Retrieved on Feb. 8, 2012.
de Bono, et al., Prednisone Plus Cabazitaxel or Mitoxantrone for Metastatic Castration-Resistant Prostate Cancer Progressing after Docetaxel Treatment: a Randomised Open-Label Trial, Lancet, vol. 376, No. 9747, (2010), pp. 1147-1154.
Galsky, et al., Cabazitaxel, Nature Reviews—Drug Discovery, vol. 9, (2010), pp. 677-678.
International Search Report for WO2011/051894 dated May 5, 2011.
Jevtana Prescribing Information, pp. 1-25, Jun. 17, 2010.
Antonarakis & Eisenberger, Phase III Trials with Docetaxel-Based Combinations for Metastatic Castration-Resistant Prostate Cancer. Time to Learn From Past Experiences, 31(14) J. Clin. Oncol., 1709-12 (2013).
Armstrong & George, New Drug Development in Metastatic Prostate Cancer, Urologic Oncol. Seminars & Orig. Invest., 430-437 (2008).
Beer et al., Double-Blinded Randomized Study of High-Dose Calcitriol Plus Docetaxel compared with Placebo Plus Docetaxel in Androgen-Independent Prostate Cancer: A Report from the ASCENT Investigators, 25(6) J. Clin. Oncol., 669-674 (2007).
Berry et al., Phase III Study of Mitoxantrone Plus Low Dose Prednisone Versus Low Dose Prednisone Alone in Patients with Asymptomatic Hormone Refractory Prostate Cancer, 168(6) J. Urol., 2439-43 (2002).
Booth et al., From the Analyst's Couch: Oncology Trials 2 Nature Reviews Drug Discovery, 609-610 (Aug. 2003).
Cabral, Factors Determining Cellular Mechanisms of Resistance to Antimitotic Drugs, 4 Drug Resistance Updates, 3-8 (2001).
Carducci et al., A Phase 3 Randomized Controlled Trial of the Efficacy and Safety of Atrasentan in Men with Metastatic Hormone-Refractory Prostate Cancer, 110(9) Cancer, 1959-66 (2007).
D'Amico, US Food and Drug Administration Approval of Drugs for the Treatment of Prostate Cancer: A New Era Has Begun, J. Clin. Oncol., 32(4) 362-364 (2014).
Di Lorenzo et al., Combination of Bevacizumab and Docetaxel in Docetaxel-Pretreated Hormone-Refractory Prostate Cancer: A Phase 2 Study, 54(5) Europ. Urol., 1089-1096 (2008).
Diéras et al., Larotaxel in Combination with Trastuzumab in Patients with HER2+ Metastatic Breast Cancer: Interim Analysis of an Open Phase II Label Study, 26 (15S) J. Clin. Oncol. (Meeting Abstracts) Suppl. 1070 (May 2008).
Diéras et al., Phase II Multicenter Study of Larotaxel (XRP9881), a Novel Taxoid, in Patients with Metastatic Breast Cancer Who Previously Received Taxane-Based Therapy, 19 Annals of Oncol., 1255-1260 (2008).
Dumontet & Sikic, Mechanisms of Action of and Resistance to Antitubulin Agents: Microtubule Dynamics, Drug Transport, and Cell Death, 17(3) J. Clin. Oncol., 1061-1070 (1999).
Halabi et al., Prostate-Specific Antigen Changes as Surrogate for Overall Survival in Men with Metastatic Castration-Resistant Prostate Cancer Treated with Second Line Therapy, 31(31) J. Clin. Oncol., 3944-50 (2013).
Higano et al., Phase 1/2 Dose-Escalation Study of a GM-CSF-Secreting, Allogeneic, Cellular Immunotherapy for Metastatic Hormone-Refractory Prostate Cancer, 113(5) Cancer, 975-984 (Sep. 1, 2008).
Kaur et al., Suramin 's Development, What Did We Learn, 20 Investigational New Drugs, 209-219 (2002).
Kola & Landis, Can the Pharmaceutical Industry Reduce Attrition Rate?, 3 Nature Reviews Drug Discovery, 711-15 (2004) (previously cited).
Mackinnon et al., Molecular Biology Underlying the Clinical Heterogeneity of Prostate Cancer: An Update, 133 (7) Arch. Pathol. Lab. Med., 1033-40 (Jul. 2009).
Michaelson et al., Randomized, Placebo-Controlled, Phase III Trial of Sunitinib Plus Prednisone Versus Prednisone Alone in Progressive, Metastatic, Castration-Resistant Prostate Cancer, 32(2) J. Clin. Oncol., 76-82 (2014).
Mulcahy, Phase 3 Trial of Immunotherapy for Metastatic Prostate Cancer Terminated, Medscape Medical News (Oct. 17, 2099), [retrieved on Jun. 26, 2014] from: http://www.medscape.com/viewarticle/582220.
Ramiah et al., Clinical Endpoints for Drug Development in Prostate Cancer, 18 Curr. Opin. Urol., 303-308 (2008).
Slovin et al., Ipilimumab Alone or in Combination with Radiotherapy in Metastatic Castration-Resistant Prostate Cancer: Results from an Open-Label, Multicenter Phase I/II Study, 24 Annals of Oncol., 1813-1828 (2013).
Small et al., Randomized Phase II Study Comparing 4 Monthly Doses of Ipilimumab (MDX-010) as a Single Agent or in Combination with a Single Dose of Docetaxel in Patients with Hormone-Refractory Prostate Cancer, 24(18S) J. Clin. Oncol. (Meeting Abstracts) S4609 (Jun. 2006).
Small et al., Granulocyte Macrophage Colony Stimulating Factor-Secreting Allogeneic Cellular Immunotherapy for Hormone-Refractory Prostate Cancer, 13 Clin. Cancer Res., 3883-3891 (2007).
Sternberg et al., Larotaxel with Cisplatin in the First-Line Treatment of Locally Advanced/Metastatic Urothelial Tract or Bladder Cancer: A Randomized, Active-Controlled, Phase III Trial, 85 Oncol., 208-215 (2013).
Susman, ASCO: Calcitriol Fails in ASCENT-2 Prostate CA Trial, MedPage Today (Jun. 9, 2010), [retrieved on Jun. 27, 2014] from: http://www.medpagetoday.com/MeetingCoverage/ASCO/20575.
Van Cutsem et al., A Phase III Study Comparing Larotaxel to 5-FU (Continuous Intravenous 5-FU or Capecitabine) in Patients with Advanced Pancreatic Cancer (APC) Previously Treated with a Gemcitabine Containing Regimen, 21 (6S) Annals of Oncol. Oral Presentations, O-0007 (Jul. 2010).
Van Hook et al., Orteronel for the Treatment of Prostate Cancer, 10(5) Future Oncol., 803-811 (2014).
Wiechec & Hanson, The Effect of Genetic Variability on Drug response in Convention Breast Cancer Treatment, 625 Eur. J. Pharmacol., 122-130 (2009).
Williams, Discontinued Drugs in 2008: Oncology Drugs, 18(11) Expert. Opin. Investig. Drugs 1581-1594 (2009).
Wirth & Froschermaier, The Antiandrogen Withdrawal Syndrome, 25 (Suppl. 2) Urol Res., S67-71 (1997).
Zatloukal et al., Randomized Multicenter Phase II Study of Larotaxel (XRP9881) in Combination with Cisplatin or Gemcitabine as First-Line Chemotherapy in Nonirradiable Stage IIIB or Stage IV Non-Small Cell Lung Cancer, 3 J. Thorac. Oncol. 894-901 (2008).
Zielinski & Chi, Custirsen (OGX-011): A Second-Generation Antisense Inhibitor of Clusterin in Development for the Treatment of Prostate Cancer, 8(1) Future Oncol., 1239-1251 (2012).

(56) References Cited

OTHER PUBLICATIONS

Novacea, Inc. SEC Form 8-K at 1.02, (2008) [retrieved on Jun. 27, 2014] from: http://www.sec.gov/Archives/edgar/data/1178711/000119312508077953/d8k.htm.
Sanofi-Aventis SEC Form 20-F (Dec. 31, 2006) at 39, [retrieved on Jun. 27, 2014] from: http://www.sec.gov/Archives/edgar/data/1121404/000119312507072848/d20f.htm.
Avastin (bevacizumab), Prescribing Information (Label) Jul. 2009.
Yervoy (ipilimurnab), Prescribing Information (Label), Dec. 2013.
A Randomized, Open-Label, Phase 3 Study of Larotaxel IV Every 3 Weeks Versus Capecitabine (Xeloda®) Tablets Twice Daily for 2 Weeks in 3-Week Cycles in Patients with Metastatic Breast Cancer (MBC) Progressing After Taxanes and Anthracycline Therapy (EFC6089) (2012), [retrieved on Jun. 27, 2014] from: http://en.sanofi.com/img/content/study/EFC6089_summary.pdf.
Bristol-Myers Squibb Reports Results for Phase 3 Trial of Yervoy® (Ipilimumab) in Previously-Treated Castration Resistant Prostate Cancer, Press Release Sep. 12, 2013 [retrieved on Jun. 27, 2014] from: http://news.bms.com/press-release/rd-news/bristol-myers-squibb-reports-results-phase-3-trial-yervoy/ipilimumab-previousl.
Clinical Trials.gov, Satraplatin in Hormone Refractory Prostate Cancer Patients Previously Treated with one Cytotoxic Chemotherapy Regimen [retrieved on Jun. 27, 2014] from: https://clinicaltrials.gov/ct2/show/NCT00069745?term=SPARC&cond=prostate&rank=3.
Clinical Trials.gov, Larotaxel every 3 weeks vs. capecitabine in patients with metastatic breast cancer progressing after taxanes and anthracycline therapy [retrieved on Jun. 24, 2014] from: https://clinicaltrials.gov/ct2/show/NCT00081796?term=larotaxel&rank=7.
Clinical Trials.gov, Larotaxel plus cisplatin vs. gemcitabine plus cisplatin in first line treatment of patients with locally advanced/metastatic bladder cancer [retrieved on Jun. 24, 2014] from: https://clinicaltrials.gov/ct2/show/NCT00625664?term=larotaxel&rank=4.
Clinical Trials.gov, Larotaxel vs. 5-FU or capecitabine in patients with pancreatic cancer previously treated with gemcitabine [retrieved on Jun. 24, 2014] from: https://clinicaltrials.gov/ct2/show/NCT00417209? term=larotaxel&rank=2.
Press Release: OncoGenex Announces Top-Line Survival results of Phase 3 Synergy Trial Evaluating Custirsen for Metastatic Castration-Resistant Prostate Cancer, PRNewswire Apr. 28, 2014.
Press Release: Roche Provides Update on Phase III study of Avastin in Men with Late Stage Prostate Cancer, Media Release Mar. 12, 2010 [retrieved on Jun. 27, 2014] from: http://ww.roche.com/media/media_releases/med-cor-2010-03-12.htm.
Press Release: Takeda Announces Termination of Orteronel (TAK-700) Development for Prostate Cancer in Japan, U.S.A. and Europe, Jun. 19, 2014 [retrieved on Jun. 27, 2014] from: http://www.takeda.com/news/2014/20140619_6615.html.
Jevtana NDA Clinical Overview, excerpt, (2014), pp 2-13.
Cisternino, et al., Nonlinear Accumulation in the Brain of the New Taxoid TXD258 Following Saturation of P-Glycoprotein at the Blood-Brain Barrier in Mice and Rats, British Journal of Pharmacology, (2003), vol. 138, pp. 1367-1375.
Pivot, et al., Multicenter Phase 2 Study of XRP6258 in Taxane-Resistant Metastatic Breast Cancer (MBC) Patients (pts). Breast Cancer Research and Treatment, (2005), vol. 94, No. Suppl. 1, p. S68, Abst. 1084.
Attard, et al., Update on Tubulin-Binding Agents, Pathologic Biologie, vol. 54, (2006), pp. 72-84.
Beardsley, et al., Systemic Therapy After First-Line Docetaxel in Metastic Castration-Resistant Prostate Cancer, Current Opinion in Supportive and Palliative Care, (2008), vol. 2, No. 3, pp. 161-166.
Pivot, et al., A Multicenter Phase II Study of XRP6258 Administered as a 1-h i.v. Infusion Every 3 Weeks in Taxane-Resistant Metastatic Breast Cancer Patients, Annals of Oncology, vol. 19, No. 9, pp. 1547-1552, (2008).

The National Horizon Scanning Centre of National Institute for Health Research, Cabazitaxel (XRP-6258) for Hormone Refractory, Metastatic Prostate Cancer—Second Line After Docetaxel, University of Birmingham, pp. 1-6, (2009).
Sanofi-Aventis Press Release: 2006: In a Difficult Environment, Another Year of Growth in Adjusted EPS Excluding Selected Items, (Feb. 13, 2007), pp. 1-31.
Buonerba, et al., Docetaxel Rechallenge in Castration-Resistant Prostate Cancer: Scientific Legitimacy of Common Clinical Practice, European Urology, (2010), vol. 58, No. 4, pp. 636-637.
Di Lorenzo, et al., Castration-Resistant Prostate Cancer: Current and Emerging Treatment Strategies, Drugs, (2010), vol. 70, No. 8, pp. 983-1000.
Yoo, et al., XRP6258—Induced Gene Expression Patterns in Head and Neck Cancer Carcinoma, Laryngoscope, (2010), vol. 120, No. 6, pp. 1114-1119.
Shabafrouz, et al., New Drugs at the Horizon for Men With Prostate Cancer, Revue Medicale Suisse, (2010), vol. 6, No. 250, pp. 1057-1058 & 1060-1061.
Dorff, Cabazitaxel in Prostate Cancer: Stretching a String, Lancet, (2010), vol. 376, No. 9747, pp. 1119-1120.
Bouchet, et al., Cabazitaxel, a New Taxane With Flavorable Properties, Drugs of Today, (2010), vol. 46, No. 10, pp. 735-742.
Pal, et al., Critical Appraisel of Cabazitaxel in the Management of Advanced Prostate Cancer, Clinical Interventions in Aging, (2010), vol. 5, pp. 395-402.
Sartor, et al., Improving Outcomes With Recent Advances in Chemotherapy for Castrate-Resistant Prostate Cancer, Clinical Genitourinary Cancer, (2010), vol. 8, No. 1, pp. 23-28.
Pouessel, et al., Actualities in Prostate Cancer in ASCO Annual Meeting 2010, Bulletin du Cancer. (2010), vol. 97, No. 12, pp. 1563-1572.
Richards, Improved Survival in Second-Line Advanced Prostate Cancer Treated With Cabazitaxel, Nature Reviews Clinical Oncology, (2010), vol. 7, No. 12, p. 671.
De Bono, et al., Cabazitaxel or Mitoxantrone With Prednisone in Patients With Metastatic Castration-Resistant Prostate Cancer (mCRPC) Previously Treated With Docetaxel: Final Results of a Multinational Phase III Trial (TROPIC)., 46th Annu Meet Am Soc Clin Oncol (ASCO), J. Clin. Oncology, (2010) 28:15S (Suppl), Abst 4508.
Denis, et al., Phase I and Pharmacokinetic Study of RPR116258A, A Novel Taxane Derivative, Administered Intravenously over 1 hour every 3 weeks, Clinical Cancer Research, vol. 6, (2000), (Supplement), Abstract 568, p. 4579s.
Lortholary, et al., Phase I and Pharmacokinetics (PK) Study of RPR 116258A Given as 1-hour Infusion in Patients (pts) With Advanced Solid Tumors, Clinical Cancer Research, vol. 6, (2000), (Supplement), Abstract 569, pp. 4579s-4580s.
Oudard, et al., Cabazitaxel Plus Prednisone/Prednisolone Significantly Increases Overall Survival Compared to Mitoxantrone Plus Prednisone/Prednisolone in Patients With Metastatic Castration-Resistant Prostate Cancer (MCRPC) Previously Treated With Docetaxel: Final Results With Updated Overall Survival of a Multinational Phase III Trial (TROPIC), Ann. of Oncology, vol. 21, (Suppl. 8), p. viii272, (2010), Abstract 871PD.
Kris, et al., Clinical Cancer Advances 2010: Annual Report on Progress Against Cancer From the American Society of Clinical Oncology, J Clin Oncology, (2010), vol. 28, No. 36, pp. 5327-5347, 947.
Drug Data Report, Antimitotic Drugs, (2003), vol. 25, No. 6, p. 550, (2003).
Drug Data Report, Cabazitaxel, (2010). vol. 32, No. 10, pp. 999-1017 at p. 1012.
Sanofi-Aventis Press Release: Resilient Sales and Business EPS in Q3 2010, (Oct. 28, 2010), pp. 1-24.
Sanofi-Aventis Press Release: EPS Growth in Q2 2010, (Jul. 29, 2010), pp. 1-27.
ClinicalTrials.gov, Safety and Pharmacokintic Study of Cabazitaxel in Patients With Advanced Solid Tumors and Liver Impairment, Web site, (2010), pp. 1-7 [retrieved on Jan. 6, 2014].
Sanofi-Aventis Press Release: Q1 2010: A Good First Quarter, (Apr. 29, 2010), pp. 1-19.

(56) References Cited

OTHER PUBLICATIONS

ClinicalTrials.gov, Effect of Cabazitaxel on the QTc Interval in Cancer Patients (QT-Cab), Web site, (2010) Mar. 24, pp. 1-7 [retrieved on Jan. 6, 2014].
Sanofi-Aventis Press Release: Sanofi-Aventis Delivers Double-Digit EPS Growth in 2009 as the Transformation Program Progresses, (Feb. 10, 2010), pp. 1-26.
ClinicalTrials.gov, A Study to Evaluate the Effects of Combining Cabazitaxel With Cisplatin Given Every 3 Weeks in Patients With Advanced Solid Cancer, Web Site, (Jul. 22, 2009), pp. 1-7 [retrieved on Jan. 6, 2014].
Sanofi-Aventis Press Release: Sanofi-Aventis Delivers 2008 Results Above Guidance, (2009), Feb. 11, pp. 1-27.
Numata, et al., The Preliminary Results of Docetaxel-Prednisolone Combination Therapy for the Japanese Pateients With Hormone-Refractory Prostate Cancer, Acta Urol. Jpn., vol. 53, pp. 93-97, (2007).
Miura, et al., A Case of Hormone-Refractory Prostate Cancer (HRPC) With Tumor Fever Responding to Docetaxel Plus Prednisolone Therapy, Jpn J Cancer Chemother, vol. 33, No. 6, pp. 841-844, (2006).
Shimazui, et al., Three-Weekly Docetaxel With Prednisone is Feasible for Japanese Patients With Hormone-Refractory Prostate Cancer: A Retrospective Comparative Study With Weekly Docetaxel Alone, Jpn J Clin Oncol, (2007), vol. 37, No. 8, pp. 603-808.
Kola, et al., Can the Pharmaceutical Industry Reduce Attrition Rates?, Nature Reviews Drug Discovery, vol. 3, (2004), pp. 711-715.
Dimasi, et al., Trends in Risks Associated With New Drug Development: Success Rates for Investigational Drugs, Nature, vol. 87, No. 3, pp. 272-277, (2010).
Bertold, et al., Docetaxel Plus Prednisone or Mitoxantrone Plus Prednisone for Advanced Prostate Cancer: Updated Survival in the TAX 327 Study, Journal of Clinical Oncology, vol. 26, No. 2, (2008) pp. 242-245.
Merck Index 14th 2006, No. 190, p. 36, Agomelatine.
Tan, Novel Agents in the Treatment of Hormone-Independent Metastatic Prostate Cancer, Actas Urol Esp., (2007), vol. 31, No. 6, pp. 660-685 (followed by non-verified English translation).
El Docetaxel Asociado a la Prednisona Mejora et Cancer de Prostate, [Retrieved from the internet on Oct. 26, 2012] Retrieved from http://www.rnedicinageriatrica.com.ar/viewnews.php?id=EEpVVFZVppsBCjOavj.
Dres, et al., Treatment alternatives for advanced prostate cancer, [Retrieved from the internet on Jul. 29, 2014] Retrieved from http://www.intramed.net/contenidover.asp?contenidoID=37957 (followed by non-verified English translation).
Taxotere (Docetaxel) Mejora Significativamente la Supervivencia de los Pacientes con Cancer de Prostate Avanzado, PMFARMA Espana, (2007).
Docetexel Reduce el Riesgo de Muerte en Pacientes con Cancer de Prostate Metastatico Androgeno Independiente, [Retrieved from the internet on Jul. 29, 2014]. Retrieved from http://www.intramed.net/contenidover.asp?contenidoID=31823 (followed by non-verified English translation).
Cancer de Prostata Diseminado, Quimioterapia. [Retrieved from the internet on Jul. 29, 2014]. Retrieved from http://www.guiasalud.es/egpc/cancer_prostata/resumida/apartado06/otros02.html, pp. 1-9.
Revision Sistematica y Modelo Economico de Efectividad Clinica y Coste-Efectividad de Docetaxel en Combinacion con Prednisona/Prednisolona para el Tratamiento de Cancer de Prostata Metastasico Refractario a Hormonas, [Retrieved from the internet on Jul. 29, 2014]. Retrieved from http://www.sefh.es/sefnboletin/vernoticiaboletin.php?id=2663.
Figg et al., Cabazitaxel Filling One of the Gaps in the Treatment of prostate Cancer. Cancer Biology & Therapy, vol. 10. No. 12, pp. 1233-1234, (2010).
Mirtsching, Prostate Cancer Clinical Trials in Dallas; Texas Area. [Retrieved from the Internet on Aug. 19, 2014]. Retrieved from http://www.healthcentral.com/prostate/c/5618/14589/dallas-texas-area, pp. 3-4.

\* cited by examiner

ANTITUMORAL USE OF CABAZITAXEL

CROSS-REFERENCE TO RELATED APPLICATIONS

This application is a continuation of International Application No. PCT/IB2010/054866, filed Oct. 27, 2010, which claims the benefit of priority of U.S. Provisional Application No. 61/256,160, filed Oct. 29, 2009, U.S. Provisional Application No. 61/293,903, filed Jan. 11, 2010, U.S. Provisional Application No. 61/355,834, filed Jun. 17, 2010, U.S. Provisional Application No. 61/355,888, filed Jun. 17, 2010, U.S. Provisional Application No. 61/369,929, filed Aug. 2, 2010, U.S. Provisional Application No. 61/383,933, filed Sep. 17, 2010, and U.S. Provisional Application No. 61/389,969, filed Oct. 5, 2010, all of which are incorporated herein by reference.

The present invention relates to a novel antitumoral use of cabazitaxel in the treatment of prostate cancer, which may be metastatic, especially for patients who are not catered for by a taxane-based treatment. In particular, the present invention relates to the use of cabazitaxel in the treatment of patients with castration resistant metastatic prostate cancer, who have been previously treated with a docetaxel based regimen, an unmet medical need.

BACKGROUND

Prostate cancer affects a large proportion of the male population worldwide: 680 000 cases worldwide in 2002; it is predicted that there will be 900 000 new cases per year up to 2010 (CA Cancer J. Clin., 2005, 55, 74-108). It is the most frequently occurring cancer in men after lung cancer.

Prostate cancer is generally treated at the start by depriving the androgenic hormones, i.e. by surgical excision of the testicles The Current State of Hormonal Therapy for Prostate Cancer CA Cancer J. Clin., May 2002; 52: 154-179, or by radiotherapy treatment External beam radiation therapy for prostate cancer CA Cancer J. Clin., November 2000; 50: 349-375. Treatments with antiandrogens or hormone manipulations are associated with responses of short duration and without any improvement in the survival time.

The use of cytotoxic chemotherapy is not a routine treatment, whereas its role in alleviating the symptoms and reducing the levels of PSA (prostate-specific antigen) is established. No monotherapy has obtained a degree of response of greater than 30%; combinations with an effect on PSA levels were tested. No effect on the survival time was seen and, what is more, the toxicity of these treatments, particularly on elderly patients, is problematic since, in addition to their tumour, they are generally suffering from related health problems and have a limited reserve of bone marrow.

Until recently, the chemotherapies used were limited to cyclophosphamide, anthracyclines (doxorubicin or mitoxantrone) and estramustine, and the effects of these treatments are relatively mediocre. Palliative effects were observed in patients following the administration of corticoids alone or of mitoxantrone with either prednisone or hydrocortisone. Following Phase II trials, the combination of mitoxantrone with corticoids was recognized as the reference treatment for hormone-resistant prostate cancer. More recently, treatments with docetaxel in combination with estramustine or prednisone have made it possible to treat cancers that are resistant to hormone deprivation Advances in Prostate Cancer Chemotherapy: A New Era Begins CA Cancer J. Clin., September 2005; 55: 300-318, the survival was improved by 2.4 months.

It is generally accepted that the responses in advanced prostate cancers are difficult to evaluate on account of the heterogeneity of the disease and the lack of consensus regarding the treatment response criteria. Many patients with metastatic prostate cancer have no measurable disease, but have symptoms dominated by bone metastases. Measurement of the PSA level has been found to be a means for evaluating novel candidates and also the measurement of the tumour when this is possible, the measurement of bone tumours, the quality of life and the measurement of the pain.

Furthermore, cancer may become resistant to the agents used, in particular to taxanes, which limits the possible treatment options. Several taxane resistance mechanisms have been described (expression of P-glycoprotein P-gp, mdr-1 gene, modified metabolism of taxane, mutation of the tubulin gene, etc.): see Drug Resistance Updates 2001, 4(1), 3-8; J. Clin. Onc. 1999, 17(3), 1061-1070.

The technical problem that the invention intends to solve is that of providing a novel therapeutic option for treating prostate cancer, especially for patients who are not catered for by a taxane-based treatment, such as patients with castration resistant metastatic prostate cancer who have been previously treated with docetaxel (sold under the brand name Taxotere®) based regimen, an unmet medical need.

Four clinical trials on cabazitaxel are known since April 2006. Three monotherapy tests have made it possible to determine the maximum tolerated dose and the toxicities at the limit doses: these tests were performed on breast, sarcoma and prostate tumours. Doses of 10-30 mg/m² every three hours were used. A phase II trial was performed on patients with a breast cancer, who had previously received taxanes and anthracyclines as adjuvant (i.e. after a surgery) or as a first-line treatment. The response levels were 14.6% as adjuvant and 9.5% as second-line treatment.

SUMMARY

The invention relates to a novel antitumoral pharmaceutical therapeutic use comprising cabazitaxel of formula

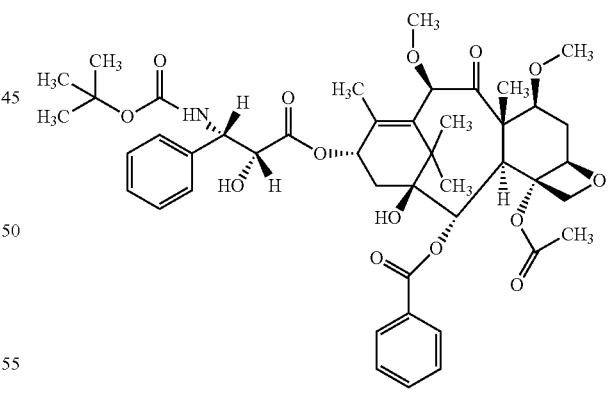

The invention also relates to methods of treating patients with prostate cancer comprising administering an effective amount of the antitumoral agent cabazitaxel to said patient.

This antitumoral agent may be in the form of anhydrous base, a hydrate or a solvate, intended for treating prostate cancer, in particular for treating patients who are not catered for by a taxane-based treatment, such as patients who have been previously treated with a docetaxel-based regimen. This compound is preferably administered to a patient with advanced metastatic disease. In particular, the compound is administered to a patient with castration resistant prostate cancer. Cabazitaxel is preferably administered in combination with a corticoid chosen especially from prednisone and prednisolone. This corticoid is preferably administered at a daily dose of 10 mg orally.

In some aspects of the invention, cabazitaxel is administered in combination with prednisone for its use as a medicament in the treatment of patients with hormone-refractory prostate cancer who have been previously treated with docetaxel based regimen.

In some aspects of the invention, cabazitaxel is administered at a dose (defined for each administration) of between 20 and 25 mg/m². Cabazitaxel may be in the form of an acetone solvate. More particularly, the acetone solvate of cabazitaxel contains between 5% and 8% and preferably between 5% and 7% by weight of acetone.

In some aspects of the invention, cabazitaxel may be administered by intravenous infusion at a dose of between 15 and 25 mg/m², this administration cycle of the antitumour agent being repeated at an interval of 3 weeks between each cabazitaxel administration, which interval may be prolonged by 1 to 2 weeks depending on the tolerance to the preceding cabazitaxel administration.

In some embodiments, the effective amount of cabazitaxel produces at least one therapeutic effect selected from the group consisting of increase in overall survival, partial response, reduction in tumor size, reduction in metastasis, complete remission, partial remission, stable disease, or complete response.

The present invention also relates to a pharmaceutical composition that treats patients with prostate cancer comprising a clinically proven safe and effective amount of cabazitaxel.

Further embodiments of the invention comprise methods or using, treating, promoting, and providing cabazitaxel.

The present invention also relates to packages and articles of manufacture.

DETAILED DESCRIPTION

Definitions

Figure 1:
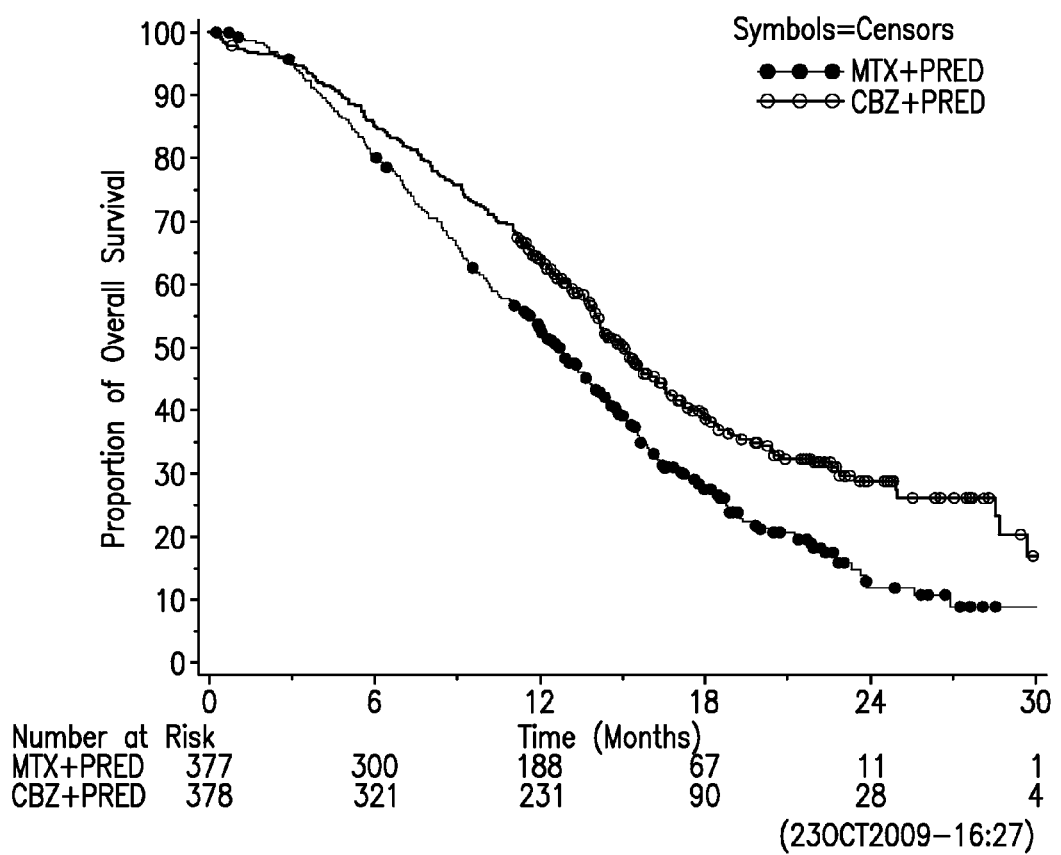
FIG. 1 displays the Kaplan-Meier curves of the overall survival in a cabazitaxel study.

Effective amount, as used herein, means an amount of a pharmaceutical compound, such as cabazitaxel, that produces an effect on the cancer to be treated.

Clinically proven, as used herein, means clinical efficacy results that are sufficient to meet FDA approval standards.

Castration resistant prostate cancer, as used herein, is synonymous with hormone-refractory prostate cancer.

"Patient," as used herein, includes both human and animals. In one embodiment, a patient is a human.

Cabazitaxel belongs to the taxoid family and has the formula:

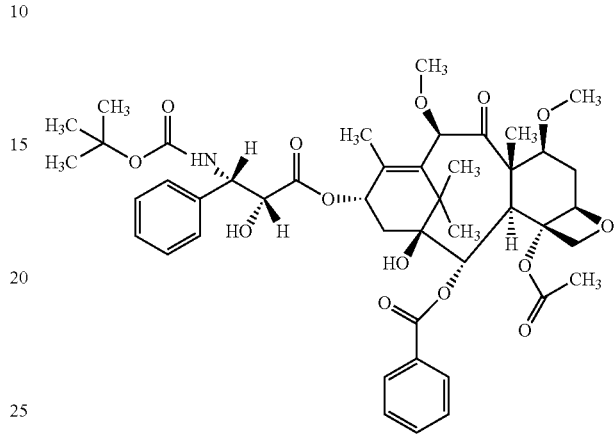

The chemical name of cabazitaxel is 4α-acetoxy-2α-benzoyloxy-5β,20-epoxy-1β-hydroxy-7β,10β-dimethoxy-9-oxo-11-taxen-13α-yl (2R,3S)-3-tert-butoxycarbonyl-amino-2-hydroxy-3-phenylpropionate. Cabazitaxel is synonymously known as (2α,5β,7β,10β,13α)-4-acetoxy-13-({(2R,3S)-3-[(tertbutoxycarbonyl)amino]-2-hydroxy-3-phenylpropanoyl}oxy)-1-hydroxy-7,10-dimethoxy-9-oxo-5,20-epoxytax-11-en-2-yl benzoate.

This compound and a preparative method thereof is described in WO 96/30355, EP 0 817 779 B1 and U.S. Pat. No. 5,847,170, which are hereby incorporated herein by reference.

Cabazitaxel may be administered in base form (cf. above formula), or in the form of a hydrate. It may also be a solvate, i.e. a molecular complex characterized by the incorporation of the crystallization solvent into the crystal of the molecule of the active principle (see in this respect page 1276 of J. Pharm. Sci. 1975, 64(8), 1269-1288). In particular, it may be an acetone solvate, and, more particularly, may be the solvate described in WO 2005/028462. It may be an acetone solvate of cabazitaxel containing between 5% and 8% and preferably between 5% and 7% by weight of acetone (% means content of acetone/content of acetone+cabazitaxel×100). An average value of the acetone content is 7%, which approximately represents the acetone stoichiometry, which is 6.5% for a solvate containing one molecule of acetone. The procedure described below allows the preparation of an acetone solvate of cabazitaxel:

940 ml of purified water are added at 20±5° C. (room temperature) to a solution of 207 g of 4α-acetoxy-2α-benzoyloxy-5β,20-epoxy-1β-hydroxy-7β,10β-dimethoxy-9-oxo-11-taxen-13α-yl (2R,3S)-3-tert-butoxycarbonylamino-2-hydroxy-3-phenylpropionate at about 92% by weight in about 2 liters of acetone, followed by seeding with a suspension of 2 g of 4α-acetoxy-2α-benzoyloxy-5β,20-epoxy-1β-hydroxy-7β,10β-dimethoxy-9-oxo-11-taxen-13α-yl (2R,3S)-3-tert-butoxycarbonylamino-2-hydroxy-3-phenylpropionate isolated from acetone/water in a mixture of 20 ml of water and 20 ml of acetone. The resulting mixture is stirred for about 10 to 22 hours, and 1.5 liters of purified water are added over 4 to 5 hours. This mixture is stirred for 60 to 90 minutes, and the suspension is then filtered under reduced pressure. The cake is washed on the filter with a solution prepared from 450 ml of acetone and 550 ml of purified water, and then oven-dried at 55° C. under reduced pressure (0.7 kPa) for 4 hours. 197 g of 4α-acetoxy-2α-benzoyloxy-5β,20-epoxy-1β-hydroxy-7β,10β-dimethoxy-9-oxo-11-taxen-13α-yl (2R,3S)-3-tert-butoxycarbonylamino-2-hydroxy-3-phenylpropionate acetone containing 0.1% water and 7.2% acetone (theoretical amount: 6.5% for a stoichiometric solvate) are obtained.

Cabazitaxel may be administered parenterally, such as via intravenous administration. A galenical form of cabazitaxel suitable for administration by intravenous infusion is that in which the cabazitaxel is dissolved in water in the presence of excipients chosen from surfactants, cosolvents, glucose or sodium chloride, etc. For example, a galenical form of cabazitaxel may be prepared by diluting a premix solution of cabazitaxel contained in a sterile vial (80 mg of cabazitaxel+2 ml of solvent+Polysorbate 80) with a sterile vial containing a solution of 6 ml of water and ethanol (13% by weight of 95% ethanol) in order to obtain 8 ml of a solution ready to be rediluted in a perfusion bag. The concentration of cabazitaxel in this ready-to-redilute solution is about 10 mg/ml. The perfusion is then prepared by injecting the appropriate amount of this ready-to-redilute solution into the perfusion bag containing water and glucose (about 5%) or sodium chloride (about 0.9%).

Cabazitaxel may be administered in combination with a corticoid, such as prednisone or prednisolone, as two distinct pharmaceutical preparations.

Accordingly, one aspect of the invention is a method of treating prostate cancer comprising administering to a patient in need thereof an effective amount of cabazitaxel in combination with a corticoid, such as prednisone or prednisolone.

The combination is administered repeatedly according to a protocol that depends on the patient to be treated (age, weight, treatment history, etc.), which can be determined by a skilled physician. In one aspect of the invention, cabazitaxel is administered by perfusion to the patient according to an intermittent program with an interval between each administration of 3 weeks, which may be prolonged by 1 to 2 weeks depending on the tolerance to the preceding administration. The median number of cycles is 6. The prednisone or prednisolone may be administered daily, for example in the form of one dosage intake per day, throughout the duration of the treatment. Examples of doses for the two antitumoral agents are given in the "Example" section. The currently recommended dose is 25 mg/m$^2$ of cabazitaxel administered as a on-hour infusion and 10 mg per day of prednisone or prednisolone administered orally.

In some aspects of the invention, the patient to be treated has prostate cancer that is resistant to hormone therapy (i.e., hormone refractory) and has previously been treated with docetaxel. In some aspects, the patient has prostate cancer that progressed during or after treatment with docetaxel. In some aspects, the patient was previously treated with at least 225 mg/m$^2$ cumulative dose of docetaxel. In a particular aspect, the patient showed progression of their disease in the six months following hormone therapy or during docetaxel treatment or after docetaxel treatment. In another particular aspect, the patient showed progression of their disease in the three months following hormone therapy or after docetaxel treatment.

In some aspects of the invention, the patient to be treated has a measurable tumour and may show progression of the disease via a metastatic lesion of the viscera or of a soft tissue of at least 1 cm determined by MRI or by an axial tomographic scan (CT scan).

In some aspects of the invention, the patient to be treated has an unmeasurable tumour and may show an increase in the PSA level with three measurements at a 1-week interval or the appearance of new lesions.

In some aspects of the invention, the patient to be treated has undergone castration by orchidectomy or with LHRH agonists, elimination of the androgens or monotherapy with estramustine.

In a preferred aspect, the life expectancy of the patient to be treated should be at least 2 months.

In some aspects, the treatment does not include patients who have previously received mitoxantrone, or who have received less than 225 mg/m$^2$ of docetaxel, or who have undergone a radiotherapy that has eliminated more than 40% of the marrow, who have received a treatment within the 4 weeks preceding the test, who have a neuropathy or a stomatitis, involving the brain or the meninges, who have shown severe hypersensitivity to polysorbate or to prednisone, whose blood analysis shows an appreciable decrease in neutrophils, haemoglobin or platelets, an increase in bilirubin and/or liver enzymes and creatinine, or who have heart problems or an infection requiring antibiotics.

An aspect of the invention comprises increasing the survival of a patient with hormone refractory metastatic prostate cancer, comprising administering a clinically proven effective amount of cabazitaxel to the patient in combination with prednisone or prednisolone. In a particular aspect, the patient has previously been treated with a docetaxel-containing regimen.

Cabazitaxel may be administered in combination with a medication to prevent or control nausea and vomiting or to prevent or control hypersensitivity to the cabazitaxel treatment. Preferably, a patient is pre-medicated with the medication, for example, at least 30 minutes prior to administering each dose of cabazitaxel.

One aspect of the invention comprises a method of reducing the risk of a severe hypersensitivity reaction in a patient with prostate cancer being treated with cabazitaxel, comprising administering to the patient a medication to prevent hypersensitivity prior to the administration of cabazitaxel.

Severe hypersensitivity reactions to cabazitaxel can occur and may include generalized rash/erythema, hypotension and bronchospasm. Patients should be observed closely for hypersensitivity reactions, especially during the first and second infusions. Hypersensitivity reactions may occur within a few minutes following the initiation of the infusion of cabazitaxel, thus facilities and equipment for the treatment of hypotension and bronchospasm should be available. If severe hypersensitivity reaction occurs, cabazitaxel infusion should be immediately discontinued and appropriate therapy should be administered. Examples of medications which may be used to prevent hypersensitivity to the cabazitaxel treatment include antihistamines, such as dexchlorpheniramine (for example 5 mg), and diphenhydramine (for example 25 mg) or equivalent antihistamines; and corticosteroids, such as dexamethasone (for example 8 mg) or an equivalent steroid.

Nevertheless, cabazitaxel should not be given to and may be contraindicated in patients who have a history of severe hypersensitivity reactions to cabazitaxel. Depending on the formulation administered, cabazitaxel may also be contraindicated in patients who have a history of hypersensitivity reactions to other drugs formulated with polysorbate 80.

One aspect of the invention comprises an article of manufacture comprising:
  a) a packaging material;
  b) cabazitaxel, and
  c) a label or package insert contained within the packaging material indicating that severe hypersensitivity reactions can occur.

Gastrointestinal symptoms, such as, for example nausea, vomiting, and diarrhea, may occur with the treatment of cabazitaxel. Mortality related to diarrhea and electrolyte imbalance has been reported. Therefore, patients may also be rehydrated and treated with anti-diarrheal or anti-emetic medications as needed. Treatment delay or dosage reduction may be necessary if patients experience Grade≥3 diarrhea.

Accordingly, the methods of the invention include administering a medication to prevent hypersensitivity or a medication to prevent or control nausea and vomiting in combination with cabazitaxel.

Examples of medications which may be used to prevent or control nausea and vomiting include histamine $H_2$ antagonists and antiemetics, such as ondansetron, granisetron and dolesetron.

A possible side effect of the treatment with cabazitaxel is neutropenia, which is characterized by a reduced number of neutrophils. Unfortunately, a number of neutropenia deaths have been reported. Therefore, frequent blood counts should be obtained or performed to monitor for neutropenia. If neutropenia occurs, cabazitaxel treatment may be discontinued, and restarted when neutrophil counts recover to a level of >1,500/mm$^3$. Cabazitaxel should not be given to a patient with a neutrophil count≤1,500 cells/mm$^3$.

The present invention therefore also relates to a method of treating prostate cancer with cabazitaxel comprising administering cabazitaxel to the patient, monitoring blood counts in the patient, and measuring neutrophil levels. In one aspect, the method further comprises discontinuing cabazitaxel treatment if neutropenia occurs, and optionally restarting cabazitaxel treatment when neutrophil counts recover to a level of >1,500/mm$^3$. In one aspect, the monitoring comprises taking a blood sample from the patient.

Determining neutrophil counts can be performed according to procedures well know to those skilled in the art.

One aspect of the invention is a method of reducing the risk of neutropenia complications comprising administering cabazitaxel in combination with an agent useful for treating neutropenia. Such a neutropenia treatment agent is, for example, a hematopoietic growth factor which regulates the production and function of neutrophils such as a human granulocyte colony stimulating factor, (G-CSF). In a particular aspect of the invention, the neutropenia is complicated neutropenia. Complicated neutropenia includes febrile neutropenia, prolonged neutropenia, or neutropenic infection. In a preferred embodiment, the neutropenia treatment agent is administered prior to the administration of cabazitaxel.

A particular aspect of the invention comprises a method of reducing the risk of neutropenia complications in a patient with prostate cancer being treated with cabazitaxel, comprising monitoring blood counts in the patient at regular intervals during treatment of the patient with cabazitaxel; reducing the dose of cabazitaxel if the patient experiences febrile neutropenia or prolonged neutropenia; discontinuing cabazitaxel treatment if the patient's neutrophil count is ≤1,500 cells/mm$^3$; and optionally restarting cabazitaxel treatment when the patient's neutrophil counts recover to a level≥1,500 cells/mm$^3$.

In a particular aspect, primary prophylaxis with G-CSF should be considered in patients with high-risk clinical features (age>65 years, poor performance status, previous episodes of febrile neutropenia, extensive prior radiation ports, poor nutritional status, or other serious co-morbidities) that predispose them to increased complications from prolonged neutropenia. Therapeutic use of G-CSF and secondary prophylaxis should be considered in all patients considered to be at increased risk for neutropenia complications.

In another aspect, the monitoring of complete blood counts is performed on a weekly basis during cycle 1 and before each treatment cycle thereafter so that the dose can be adjusted, if needed. Therefore, another aspect for reducing the risk of neutropenia complications comprises, monitoring blood counts in the patient and adjusting the dose of cabazitaxel. An example of a dose modification is described in Example 2.

One aspect of the invention comprises an article of manufacture comprising:
  a) a packaging material;
  b) cabazitaxel, and
  c) a label or package insert contained within the packaging material indicating that cabazitaxel should not be given to patients with neutrophil counts of ≤1,500 cells/mm$^3$.

Cases of renal failure should be identified and managed aggressively, accordingly to procedures known to those skilled in the art. Renal failure may be associated with sepsis, dehydration, or obstructive uropathy. Furthermore, impaired hepatic function (e.g., total bilirubin≥ULN, or AST and/or ALT≥1.5×ULN) may increase cabazitaxel concentrations, and cabazitaxel should not be given to patients with hepatic impairment.

Cabazitaxel may cause fetal harm when administered to a pregnant woman.

Prednisone or prednisolone administered at 10 mg daily does not affect the pharmacokinetics of cabazitaxel.

Cabazitaxel is primarily metabolized through CYP3A. Concomitant administration of strong CYP3A inhibitors (for example, ketoconazole, itraconazole, clarithromycin, atazanavir, indinavir, nefazodone, nelfinavir, ritonavir, saquinavir, telithromycin, voriconazole) may increase cabazitaxel concentrations. Therefore co-administration of cabazitaxel with strong CYP3A inhibitors should be avoided. Caution should be exercised with concomitant use of moderate CYP3A inhibitors. One aspect of the invention is a method of treating a patient for prostate cancer comprising determining whether the patient is undergoing treatment with a CYP3A inhibitor, discontinuing treatment with a CYP3A inhibitor, and then administering cabazitaxel to the patient.

Concomitant administration of strong CYP3A inducer (e.g., phenyloin, carbamazepine, rifampin, rifabutin, rifapentin, phenobarbital) may decrease cabazitaxel concentrations. Therefore co-administration of cabazitaxel with strong CYP3A inducers should be avoided. Therefore, one aspect of the invention is a method of treating a patient for prostate cancer comprising determining whether the patient is undergoing treatment with a CYP3A inducer, discontinuing treatment with a CYP3A inducer, and administering cabazitaxel to the patient.

In addition, patients should also refrain from taking St. John's Wort.

In some aspects of the invention, the cabazitaxel is administered in an amount to provide an AUC of about 991 ng·h/mL (CV 34%).

In some aspects of the invention, the cabazitaxel is administered in an amount to provide an $C_{max}$ of about 226 ng·h/mL (CV 107%).

In some aspects of the invention, the cabazitaxel is administered in an amount to provide a plasma clearance of 48.5 L/h (CV 39%).

One aspect of the invention is a package comprising cabazitaxel and a label, in a position which is visible to prospective purchasers, comprising a printed statement which informs prospective purchasers that the mean $C_{max}$ of cabazitaxel in patients with metastatic prostate cancer was 226 ng/mL (CV 107%).

Another aspect of the invention is a package comprising cabazitaxel and a label, in a position which is visible to prospective purchasers, comprising a printed statement which informs prospective purchasers that the mean AUC of cabazitaxel in patients with metastatic prostate cancer was 991 ng·h/mL (CV 34%).

Another aspect of the invention is a package comprising cabazitaxel and a label, in a position which is visible to prospective purchasers, comprising a printed statement which informs prospective purchasers that cabazitaxel has a plasma clearance of 48.5 L/h (CV 39%).

A variety of educational materials may be employed to ensure proper prescribing, dispensing, and patient compliance according to the methods described herein. For example, a variety of literature and other materials, such as, for example, prescribing information, package inserts, medications guides, physician information sheets, healthcare professional information sheets, medical journal advertisements, and product websites may describe the risks and benefits of taking cabazitaxel.

The invention also concerns a package comprising cabazitaxel and a label, said label comprising one or more messages that:
  a) the efficacy and safety of cabazitaxel in combination with prednisone were evaluated in patients with hormone refractory metastatic prostate cancer previously treated with a docetaxel containing regimen; or
  b) a total of 755 patients were randomized to receive either cabazitaxel 25 mg/m$^3$ every 3 weeks for a maximum of 10 cycles with prednisone mg orally daily, or to receive mitoxantrone 12 mg/m$^2$ intravenously every 3 weeks for a maximum of 10 cycles with prednisone 10 mg orally daily; or
  c) the median number of cycles was 6 in the cabazitaxel group and 4 in the mitoxantrone group.

The invention also concerns a package comprising cabazitaxel and a label, said label comprising one or more messages that:
  a) neutropenic deaths have been reported; or
  b) frequent blood counts should be obtained to monitor for neutropenia; or
  c) cabazitaxel should not be given if neutrophil counts are ≤1,500 cells/mm$^3$.

The invention also concerns a method of promoting the use of cabazitaxel the method comprising the step of conveying to a recipient at least one message selected from:
  a) neutropenic deaths have been reported; or
  b) frequent blood counts should be obtained to monitor for neutropenia; or
  c) cabazitaxel should not be given if neutrophil counts are ≤1,500 cells/mm$^3$;
  d) severe hypersensitivity can occur; or
  e) severe hypersensitivity can occur and may include generalized rash/erythema, hypotension and brochospasm; or
  f) discontinue cabazitaxel immediately if severe reactions occur; or
  g) discontinue cabazitaxel immediately if severe reactions occur and administer appropriate therapy; or
  h) cabazitaxel is contraindicated in patients with a history of severe hypersensitivity reactions to cabazitaxel or drugs formulated with polysorbate 80.

The invention also concerns a method of providing cabazitaxel, wherein said cabazitaxel is provided along with information indicating that:
  a) neutropenic deaths have been reported; or
  b) frequent blood counts should be obtained to monitor for neutropenia; or
  c) cabazitaxel should not be given if neutrophil counts are ≤1,500 cells/mm$^3$;
  d) severe hypersensitivity can occur; or
  e) severe hypersensitivity can occur and may include generalized rash/erythema, hypotension and brochospasm; or
  f) discontinue cabazitaxel immediately if severe reactions occur; or
  g) discontinue cabazitaxel immediately if severe reactions occur and administer appropriate therapy; or
  h) cabazitaxel is contraindicated in patients with a history of severe hypersensitivity reactions to cabazitaxel or drugs formulated with polysorbate 80.

Example 1

A clinical study was performed wherein patients received either treatment with cabazitaxel or the reference treatment based on mitoxantrone each combined with prednisone or prednisolone.

More specifically, patients over 18 years of age with metastatic castration resistant metastatic prostate cancer either measurable by RECIST criteria or non-measurable disease with rising PSA levels or appearance of new lesions, ECOG (Eastern Cooperative Oncology Group) performance stage 0-2, and adequate organ function (patients had to have neutrophils>1,500 cells/mm$^3$, platelets>100,000 cells/mm$^3$, hemoglobin>10 g/dL, creatinine<1.5× upper limit of normal (ULN), total bilirubin<1×ULN, AST<1.5×ULN, and ALT<1.5×ULN) who had had prior hormone therapy, chemotherapy, and radiotherapy, but had progressive during or after docetaxel treatment (cumulative dose≥225 mg/m$^2$) were randomized to 10 mg/day of prednisone with either mitoxantrone 12 mg/m$^2$ or cabazitaxel 25 mg/m$^2$, both administered every 3 weeks.

Patients with a history of congestive heart failure, or myocardial infarction within the last 6 months, or patients with uncontrolled cardiac arrhythmias, angina pectoris, and/or hypertension were not included in the study.

720 patients were planned to be included in the clinical study: 360 in each cabazitaxel+prednisone and mitoxantrone+prednisone group. Seven hundred and fifty-five patients (755) (median age 68; 84% white) were actually enrolled, 378 in the cabazitaxel and prednisone/prednisolone group and 377 in the mitoxantrone and prednisone/prednisolone group. The maximal number of treatment cycles was 10 for cabazitaxel and 10 for mitoxantrone. The median number of treatment cycles was 6 for cabazitaxel and 4 for mitoxantrone. The median prior dose of docetaxel treatment was 576 mg/m$^2$ for the cabazitaxel group and 529 mg/m$^2$ for the mitoxantrone group. Median follow-up was 12.8 months.

The measurements of the results are performed via the same tests as at inclusion. MRI and spiral computed tomographic (CT) scans are preferably used.

The results are evaluated according to the following criteria (cf RECIST guideline):

overall survival (OS): the time from inclusion to the study to the date of death complete response (CR): disappearance of the lesions partial response (PR): at least 30% reduction of the largest diameter of the lesion progression (PD): at least 20% increase in the sum of the largest diameter of the lesion or appearance of one or more new lesions stable disease (SD): reduction of the tumour insufficient to be included in PR and increase of the tumour insufficient to be included in PD.

The confirmations of the measurements are made at least 4 weeks after the response criterion has been established for the first time.

The progression-free survival (PFS) is the time from inclusion in the study and the date of progression or death when the progression is either an increase of the PSA, or of the tumour, or of the pain.

It was found that the combination of cabazitaxel and prednisone is a well-tolerated combination with the safety profile of taxanes. At the dose investigated in this trial (LD2: 25 mg/m$^2$ cabazitaxel+10 mg/m$^2$/day prednisone), patients receiving cabazitaxel demonstrated statistically significant longer overall survival (OS) compared to mitoxantrone (p<0.0001). The hazard ratio was 0.70 (95% CI. 0.59, 0.83) in favor of cabazitaxel corresponding to a 30% reduction in risk of death. The median survival for patients in the cabazitaxel group was 15.1 months in comparison to 12.7 months in the mitoxantrone group. Notably, the extension of survival was observed irrespective of ECOG performance status, number of prior chemotherapy regimens and age. Benefit was also seen in the third of patients who were docetaxel-refractory and had progressed during docetaxel therapy.

The data related to the treated patients are given in Table 1:

TABLE 1

Efficacy analysis (intention-to-treat)

| | | CbzP<br>N = 378<br>Median<br>(months) | MP<br>N = 377<br>Median<br>(months) |
|---|---|---|---|
| Overall survival | Median (months) | 15.1 | 12.7 |
| | Hazard ratio (95% CI) | 0.70 (0.59; 0.83) | |
| | p-value[1] | 0.0001 | |
| PFS | Median (months) | 2.8 | 1.4 |
| | Hazard ratio (95% CI) | 0.74 (0.64-0.86) | |
| | p-value[1] | 0.0001 | |
| Tumor response rate | | 14.4% | 4.4% |
| p-value[2] | | 0.0005 | |
| Time to Tumor (months) | Progression Median | 8.8 | 5.4 |
| | p-value | <0.001 | |
| PSA Response rate | | 39.2% | 17.8% |
| p-value[2] | | 0.0002 | |
| PSA PFS | Median (months) | 6.4 | 3.1 |
| | Hazard ratio (95% CI) | 0.75 (0.63-0.90) | |
| | p-value[1] | 0.0010 | |
| Pain Response rate | | 9.2% | 7.8% |
| p-value[2] | | 0.6526 | |

TABLE 1-continued

Efficacy analysis (intention-to-treat)

| | | CbzP<br>N = 378<br>Median<br>(months) | MP<br>N = 377<br>Median<br>(months) |
|---|---|---|---|
| Pain PFS | Median (months) | Not reached | 11.1 |
| | Hazard ratio (95% CI) | 0.91 (0.69-1.19) | |
| | p-value[1] | 0.5192 | |

[1]Log-rank test,
[2]Chi-square test
CbzP: cabazitaxel with prednisone
MP: mitoxantrone with prednisone Progression free survival (PFS) defined as the earliest progression in tumor, PSA or pain was also statistically significantly longer in the cabazitaxel group compared to the mitoxantrone group (p<0.0001, hazard ratio=0.74 (95% CI, 0.64, 0.86), and the median progression-free survival was 2.8 months versus 1.4 months. Response rates and PFS for PSA and tumor assessments were statistically significant in favor of cabazitaxel, while response rate and PFS for pain did not show a statistically significant difference.

The most frequent Grade 3/4 toxicities were neutropenia observed with a higher frequency in the cabazitaxel group with 81.7% compared to the mitoxantrone group with 58.0%. Rates of febrile neutropenia were 7.5% in the cabazitaxel group and 1.3% in the mitoxantrone group.

The most common (≥20%) grade 1-4 adverse reactions were anemia, leukopenia, neutropenia, thrombocytopenia, diarrhea, fatigue, nausea, vomiting, asthenia, and constipation.

The most common (≥5%) grade 3-4 adverse reactions in patients who received cabazitaxel were neutropenia, leukopenia, anemia, febrile neutropenia, diarrhea, fatigue, and asthenia.

Subgroup analyses by risk factors and a multivariate analysis showed that OS outcomes were consistent and robust in favor of cabazitaxel as shown in the herebelow table:

TABLE 2

| | MP | | CbzP | | |
|---|---|---|---|---|---|
| | N (%) | Median OS (mos) | N (%) | Median OS (mos) | CbzP vs MP HR (95% CI) |
| ITT | 377 (100) | 12.7 | 378 (100) | 15.1 | 0.70 (0.59-0.83) |
| PD while on D | 103 (27) | 12.0 | 113 (30) | 14.2 | 0.65 (0.47-0.90) |
| PD after last D dose, ≤3 mos | 180 (48) | 10.3 | 158 (42) | 13.9 | 0.70 (0.54-0.90) |
| PD after last D dose, >3 mos | 91 (24) | 17.7 | 103 (27) | 17.5 | 0.78 (0.53-1.14) | mos = months
D = Docetaxel

TABLE 3

Incidence of Reported Adverse Reactions[1] and Hematologic Abnormalities in ≥5% of Patients Receiving cabazitaxel in Combination with Prednisone or Mitoxantrone in Combination with Prednisone

| | Cabazitaxel 25 mg/m² every 3 weeks with prednisone 10 mg daily n = 371 | | Mitoxantrone 12 mg/m² every 3 weeks with prednisone 10 mg daily n = 371 | |
|---|---|---|---|---|
| | Grade 1-4 n (%) | Grade 3-4 n (%) | Grade 1-4 n (%) | Grade 3-4 n (%) |
| *Any Adverse Reaction* | | | | |
| *Blood and Lymphatic System Disorders* | | | | |
| Neutropenia[2] | 347 (94%) | 303 (82%) | 325 (87%) | 215 (58%) |
| Febrile Neutropenia | 27 (7%) | 27 (7%) | 5 (1%) | 5 (1%) |
| Anemia[2] | 361 (98%) | 39 (11%) | 302 (82%) | 18 (5%) |
| Leukopenia[2] | 355 (96%) | 253 (69%) | 343 (93%) | 157 (42%) |
| Thrombocytopenia[2] | 176 (48%) | 15 (4%) | 160 (43%) | 6 (2%) |
| *Cardiac Disorders* | | | | |
| Arrhythmia[3] | 18 (5%) | 4 (1%) | 6 (2%) | 1 (<1%) |
| *Gastrointestinal Disorders* | | | | |
| Diarrhea | 173 (47%) | 23 (6%) | 39 (11%) | 1 (<1%) |
| Nausea | 127 (34%) | 7 (2%) | 85 (23%) | 1 (<1%) |
| Vomiting | 83 (22%) | 6 (2%) | 38 (10%) | 0 |
| Constipation | 76 (20%) | 4 (1%) | 57 (15%) | 2 (<1%) |
| Abdominal Pain[4] | 64 (17%) | 7 (2%) | 23 (6%) | 0 |
| Dyspepsia[5] | 36 (10%) | 0 | 9 (2%) | 0 |
| *General Disorders and Administration Site Conditions* | | | | |
| Fatigue | 136 (37%) | 18 (5%) | 102 (27%) | 11 (3%) |
| Asthenia | 76 (20%) | 17 (5%) | 46 (12%) | 9 (2%) |
| Pyrexia | 45 (12%) | 4 (1%) | 23 (6%) | 1 (<1%) |
| Peripheral Edema | 34 (9%) | 2 (<1%) | 34 (9%) | 2 (<1%) |
| Mucosal Inflammation | 22 (6%) | 1 (<1%) | 10 (3%) | 1 (<1%) |
| Pain | 20 (5%) | 4 (1%) | 18 (5%) | 7 (2%) |
| *Infections and Infestations* | | | | |
| Urinary Tract Infection[6] | 29 (8%) | 6 (2%) | 12 (3%) | 4 (1%) |
| Pneumonia[7] | 12 (3%) | 9 (2%) | 4 (1%) | 3 (<1%) |
| *Investigations* | | | | |
| Weight Decreased | 32 (9%) | 0 | 28 (8%) | 1 (<1%) |
| *Metabolism and Nutrition Disorders* | | | | |
| Anorexia | 59 (16%) | 3 (<1%) | 39 (11%) | 3 (<1%) |
| Dehydration | 18 (5%) | 8 (2%) | 10 (3%) | 3 (<1%) |
| *Musculoskeletal and Connective Tissue Disorders* | | | | |
| Back Pain | 60 (16%) | 14 (4%) | 45 (12%) | 11 (3%) |
| Arthralgia | 39 (11%) | 4 (1%) | 31 (8%) | 4 (1%) |
| Pain in Extremity | 30 (8%) | 6 (2%) | 27 (7%) | 4 (1%) |
| Muscle Spasms | 27 (7%) | 0 | 10 (3%) | 0 |
| Bone Pain | 19 (5%) | 3 (<1%) | 19 (5%) | 9 (2%) |
| Musculoskeletal Pain | 18 (5%) | 2 (<1%) | 20 (5%) | 3 (<1%) |
| *Nervous System Disorders* | | | | |
| Peripheral Neuropathy[8] | 50 (13%) | 3 (<1%) | 12 (3.2%) | 3 (<1%) |
| Dysgeusia | 41 (11%) | 0 | 15 (4%) | 0 |
| Dizziness | 30 (8%) | 0 | 21 (6%) | 2 (<1%) |
| Headache | 28 (8%) | 0 | 19 (5%) | 0 |
| *Renal and Urinary Tract Disorders* | | | | |
| Hematuria | 62 (17%) | 7 (2%) | 13 (4%) | 1 (<1%) |
| Dysuria | 25 (7%) | 0 | 5 (1%) | 0 |
| *Respiratory, Thoracic and Mediastinal Disorders* | | | | |
| Dyspnea | 43 (12%) | 4 (1%) | 16 (4%) | 2 (<1%) |
| Cough | 40 (11%) | 0 | 22 (6%) | 0 |
| *Skin and Subcutaneous Tissue Disorders* | | | | |
| Alopecia | 37 (10%) | 0 | 18 (5%) | 0 |

TABLE 3-continued

Incidence of Reported Adverse Reactions[1] and Hematologic Abnormalities in ≥5% of Patients Receiving cabazitaxel in Combination with Prednisone or Mitoxantrone in Combination with Prednisone

| | Cabazitaxel 25 mg/m[2] every 3 weeks with prednisone 10 mg daily n = 371 | | Mitoxantrone 12 mg/m[2] every 3 weeks with prednisone 10 mg daily n = 371 | |
|---|---|---|---|---|
| | Grade 1-4 n (%) | Grade 3-4 n (%) | Grade 1-4 n (%) | Grade 3-4 n (%) |
| Vascular Disorders | | | | |
| Hypotension | 20 (5%) | 2 (<1%) | 9 (2%) | 1 (<1%) |
| Median Duration of Treatment | 6 cycles | | 4 cycles | |

[1]Graded using NCI CTCAE version 3
[2]Based on laboratory values, cabazitaxel: n = 369, mitoxantrone: n = 370.
[3]Includes atrial fibrillation, atrial flutter, atrial tachycardia, atrioventricular block complete, bradycardia, palpitations, supraventricular tachycardia, tachyarrhythmia, and tachycardia.
[4]Includes abdominal discomfort, abdominal pain lower, abdominal pain upper, abdominal tenderness, and GI pain.
[5]Includes gastroesophageal reflux disease and reflux gastritis.
[6]Includes urinary tract infection enterococcal and urinary tract infection fungal.
[7]Includes bronchopneumonia, lobar pneumonia, and pneumonia *klebsiella*.
[8]Includes peripheral motor neuropathy and peripheral sensory neuropathy.

TABLE 4

Patient Characteristics

| | MP (n = 377) | CBZP (n = 378) |
|---|---|---|
| Age (years) | | |
| Median [range] | 67 [47-89] | 68 [46-92] |
| ≥65 (%) | 57.0 | 64.9 |
| ECOG PS (%) | | |
| 0, 1 | 91.2 | 92.6 |
| 2 | 8.8 | 7.4 |
| PSA* (ng/mL) | | |
| Median [range] | 127.5 [2-11220] | 143.9 [2-7842] |
| Measurability of disease (%) | | |
| Measurable | 54.1 | 53.2 |
| Non-measurable | 45.9 | 46.8 |
| Disease site (%) | | |
| Bone | 87.0 | 80.2 |
| Lymph node | 44.8 | 45.0 |
| Visceral | 24.9 | 24.9 |
| Pain at Baseline, no. (%) | 168 (44.6) | 174 (46.0) |
| Previous Therapy, no. (%) | | |
| Hormonal | 375 (99.5) | 375 (99.2) |
| No. of Chemotherapy Regimens | | |
| 1 | 268 (71.1) | 260 (68.8) |
| 2 | 79 (21.0) | 94 (24.9) |
| >2 | 30 (8.0) | 24 (6.3) |
| Radiation | 222 (58.9) | 232 (61.4) |
| Surgery | 205 (54.4) | 198 (52.4) |
| Biologic Agent | 36 (9.5) | 26 (6.9) |
| Previous docetaxel regimens, n (%) | | |
| 1 | 327 (86.7) | 316 (83.6) |
| 2 | 43 (11.4) | 53 (14.0) |
| >2 | 7 (1.9) | 9 (2.4) |
| Median total previous docetaxel dose (mg/m[2]) | 529.2 | 576.6 |
| Disease progression relative to docetaxel administration, n (%) | | |
| During treatment | 104 (27.6) | 115 (30.4) |
| <3 months from last dose | 181 (48.0) | 158 (41.8) |
| ≥3 months from last dose | 90 (23.9) | 102 (27.0) |
| Unknown | 2 (0.5) | 3 (0.8) |
| Median time from last docetaxel dose to disease progression (months) | 0.7 | 0.8 |

The primary reason for treatment discontinuation in both groups was disease progression (Table 5). The median delivered relative dose intensity was 96.1% in the cabazitaxel group and 97.3% in the mitoxantrone group. In the cabazitaxel group, >75% of patients received >90% of the planned dose intensity. Overall, 5.1% of mitoxantrone treatment courses were dose reduced compared with 9.8% of cabazitaxel treatment courses; 6.3 and 7% of all treatment courses were delayed by 9 days or less, and 1.6 and 2.3% of courses were delayed by more than 9 days for mitoxantrone and cabazitaxel respectively (See Table 5).

TABLE 5

Treatment Received and Reasons for Discontinuation in the Intention-to-Treat Population.*

| | Mitoxantrone (N = 377) | Cabazitaxel (N = 378) |
|---|---|---|
| Patients receiving study treatment, no. (%) | 371 (98.4) | 371 (98.1) |
| Patients completing planned ten cycles of study treatment, no. (%) | 46 (12.2) | 105 (27.8) |

TABLE 5-continued

Treatment Received and Reasons for Discontinuation in the Intention-to-Treat Population.*

|  | Mitoxantrone (N = 377) | Cabazitaxel (N = 378) |
|---|---|---|
| Discontinuation of study treatment, no. (%) | 325 (86.2) | 266 (70.4) |
| Reasons for discontinuation of study treatment, no. (%) |  |  |
| Disease progression | 267 (70.8) | 180 (47.6) |
| Adverse event | 32 (8.5) | 67 (17.7) |
| Non-compliance with protocol | 0 | 1 (0.3) |
| Lost to follow-up | 2 (0.5) | 0 |
| Patient's request | 17 (4.5) | 8 (2.1) |
| Other | 7 (1.9) | 10 (2.7) |
| No. of treatment cycles, median (range)† | 4 (1-10) | 6 (1-10) |
| Relative dose intensity, median % (range)† | 97.3 (42.5-106.0) | 96.1 (49.0-108.2) |
| Treatment delays, no. of cycles (%)‡ |  |  |
| ≤9 days | 110 (6.3) | 157 (7.0) |
| >9 days | 28 (1.6) | 51 (2.3) |
| Dose reductions, no. of cycles (%)‡ | 88 (5.1) | 221 (9.8) |

Figure 2:
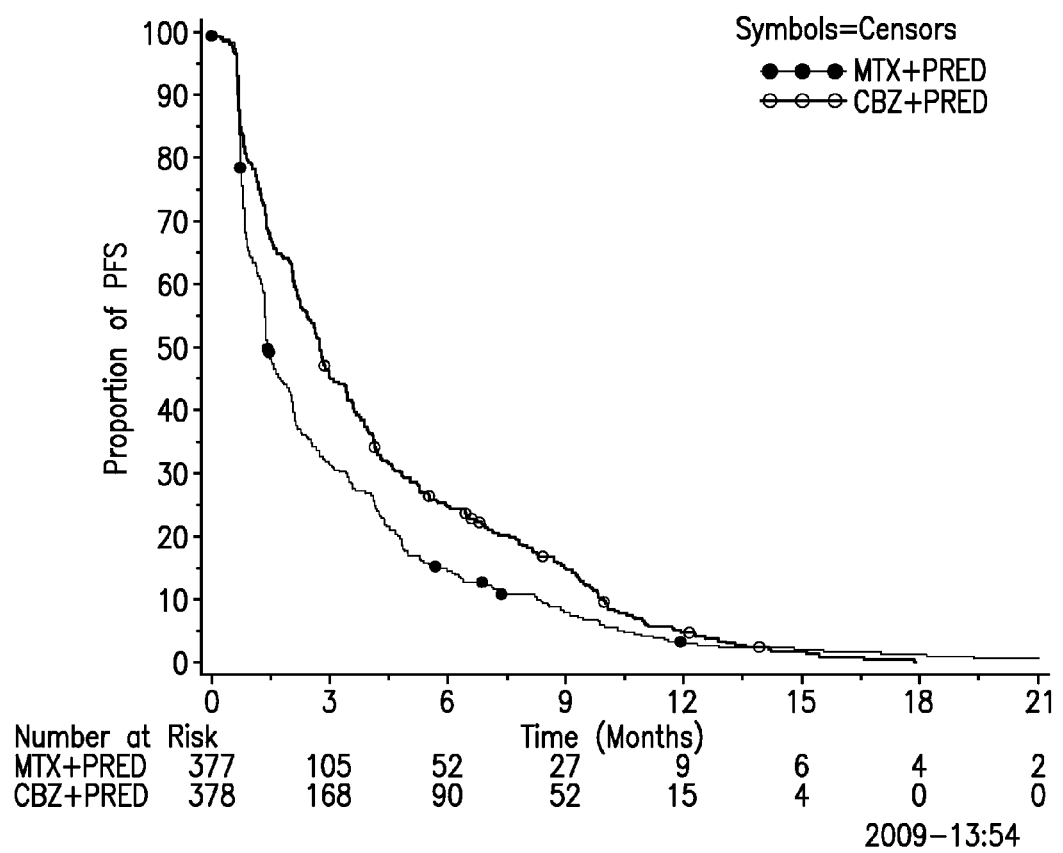
FIG. 2 displays the Kaplan-Meier curves of progression-free survival in a cabazitaxel study.
Figure 3:
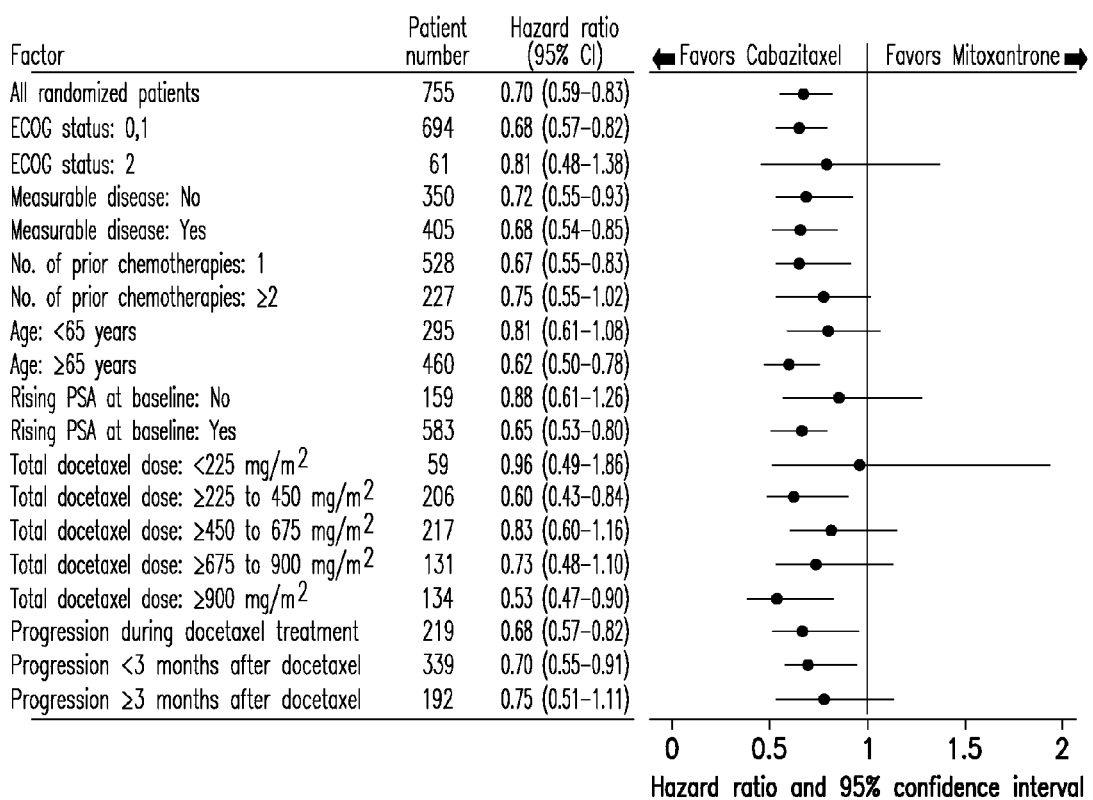
FIG. 3 shows an intention-to-treat analysis of overall survival in subgroups of patients defined by baseline characteristics. Hazard ratios<1 favor the cabazitaxel group, while those >1 favor the mitoxantrone group. CI denotes confidence intervals.

The results of this study are further illustrated to FIGS. 1, 2, and 3.

Example 2

Table 6 illustrates an example of a dosage modification for adverse reactions in patients treated with cabazitaxel

TABLE 6

| Toxicity | Dosage Modification |
|---|---|
| Prolonged grade ≥3 neutropenia (greater than 1 week) despite appropriate medication including G-CSF | Delay treatment until neutrophil count is >1,500 cells/mm³, then reduce dosage of cabazitaxel to 20 mg/m². Use G-CSF for secondary prophylaxis. |
| Febrile neutropenia | Delay treatment until improvement or resolution, and until neutrophil count is >1,500 cells/mm³, then reduce dosage of cabazitaxel to 20 mg/m². Use G-CSF for secondary prophylaxis. |
| Grade ≥3 diarrhea or persisting diarrhea despite appropriate medication, fluid and electrolytes replacement | Delay treatment until improvement or resolution, then reduce dosage of cabazitaxel to 20 mg/m². |

Discontinue cabazitaxel treatment if a patient continues to experience any of these reactions at 20 mg/m².

Example 3

Performance Status and Pain Scores During Treatment

Methods

ECOG PS, pain measures, and analgesic consumption were assessed prior to every treatment cycle and at the end of study treatment.

Pain assessments: Present Pain Intensity (PPI) scale from the McGill-Melzack questionnaire (Melzack R. Pain 1975; 1:277-99). Mean Analgesic Score (AS) derived from analgesic consumption (in morphine equivalents) was calculated for the one-week period prior to each evaluation. Area under the curve (AUC) of PPI and AS was calculated by the trapezoid formula. Cumulative AUC of PPI and AS was calculated up to the last cycle of data available for each patient. Average AUC of the treatment groups was compared from Cycle 1 to Cycle 10.

Results

Figure 4:
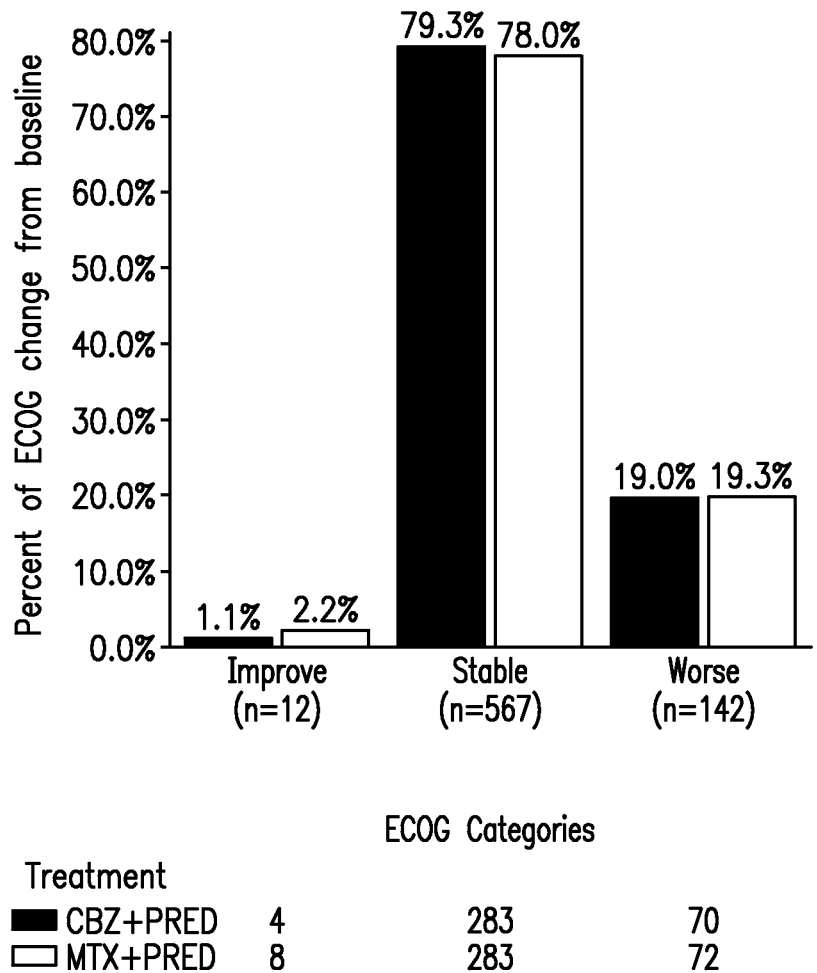
FIG. 4 graphically depicts the proportion of patients with changes in ECOG performance status from baseline during treatment (safety population). The "Improved" column represents PS2 at baseline changed to 0 or 1 during treatment. The "stable" column represents no change, and the "Worse" column represents PS2 at baseline and changed to ≥3, or 0 or 1 at baseline changed to ≥2 during treatment.

Performance status remained stable in most patients during the treatment period and was similar between groups. See FIG. 4.

Figure 5:
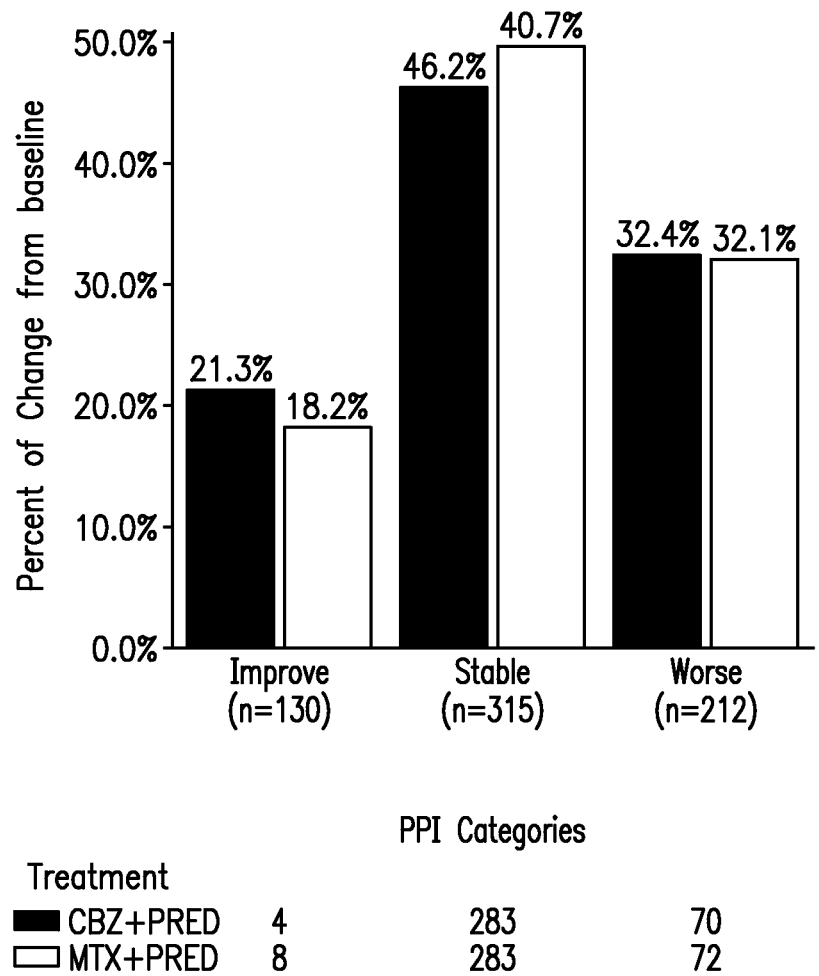
FIG. 5 graphically depicts the proportion of patients with changes from baseline in the Present Pain Intensity score during treatment (ITT). The "Improved" column represents patients in which the PPI score during treatment was lower versus baseline. The "Stable" column represents no change, and the "Worse" column represents patients with >1 unit increase in PPI score during treatment versus baseline.

Overall, PPI scores were comparable; improving from baseline in 21.3% of men in the CbzP group and 18.2% in the MP group. See FIG. 5.

Figure 6:
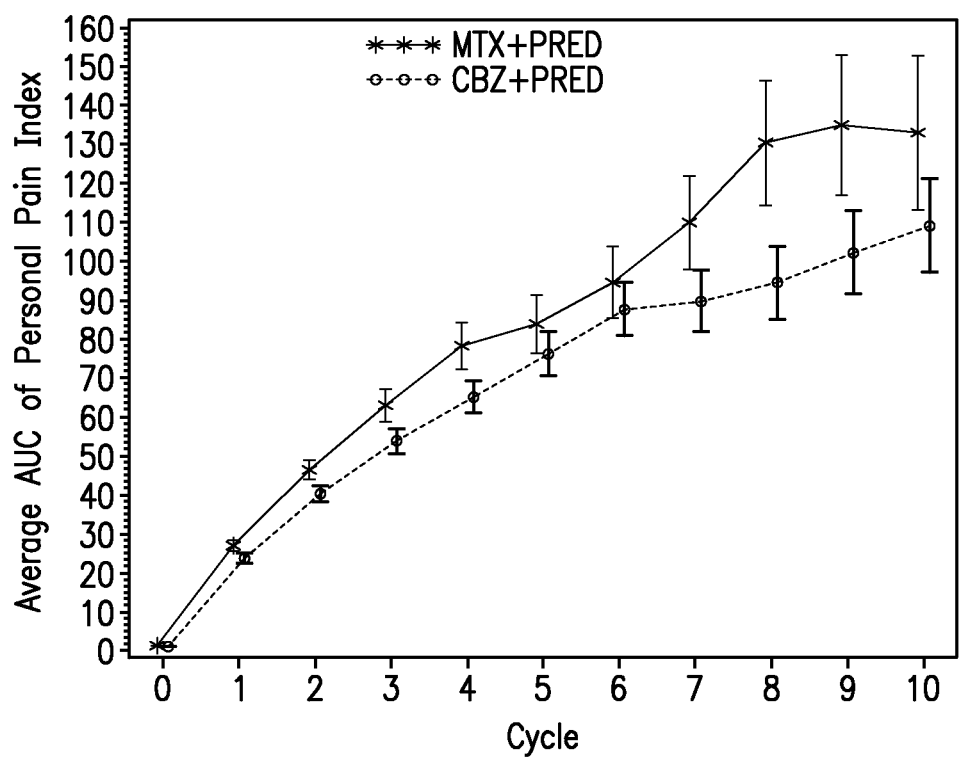
FIG. 6 graphically presents the mean area under the curve for PPI and analgesic scores by treatment cycle.

The CbzP group had a lower mean area under the curve (AUC) of PPI, suggesting less severe pain especially during cycles 7-10. See FIG. 6.

Figure 7:
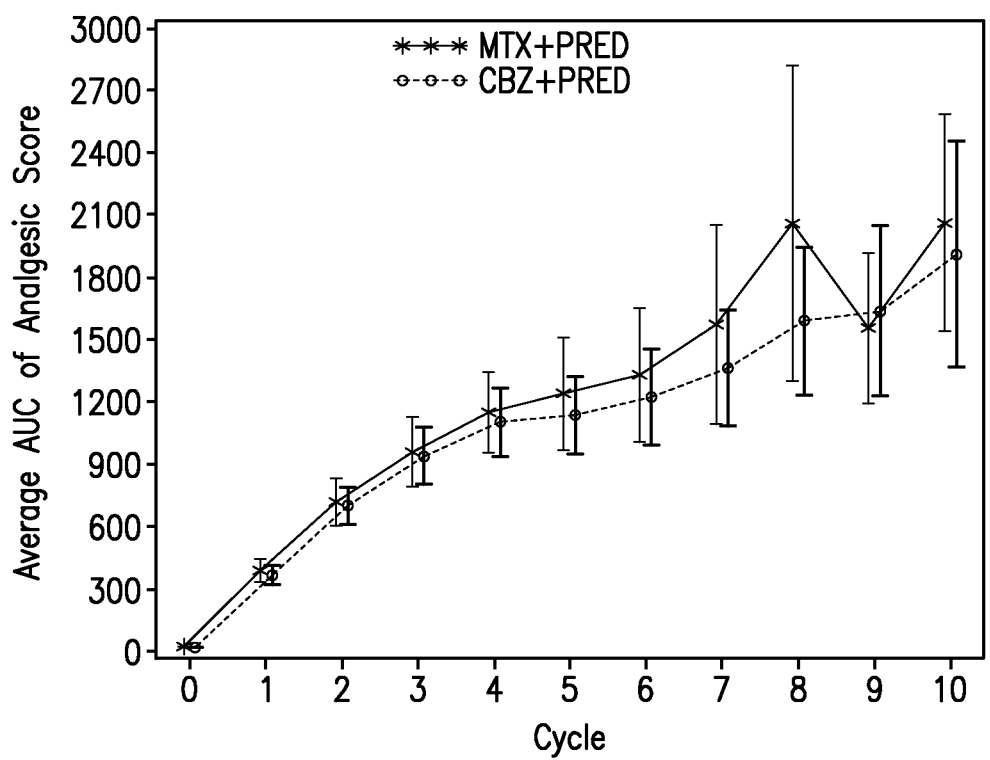
FIG. 7 graphically presents the mean AUC analgesic score.

Analgesic use was comparable between the groups (lower mean AUC of AS means lower pain medication use). See FIG. 7.

Conclusion

Despite longer treatment with CbzP no worsening in ECOG PS was seen.

Present Pain Intensity score improved in 21% of men in CbzP vs. 18% in MP arm. Assessment of pain scores suggested less severe pain in the CbzP group during treatment.

Pain medication use was similar between groups.

Example 4

A population pharmacokinetic analysis was conducted in 170 patients with solid tumors at doses ranging from 10 to 30 mg/m² weekly or every 3 weeks.

Based on the population pharmacokinetic analysis, after an intravenous dose of cabazitaxel 25 mg/m² every 3 weeks, the mean $C_{max}$ in patients with metastatic prostate cancer was 226 ng/mL (CV 107%) and was reached at the end of the 1-hour infusion ($T_{max}$). The mean AUC in patients with metastatic prostate cancer was 991 ng·h/mL (CV 34%). No major deviation from the dose proportionality was observed from 10 to 30 mg/m² in patients with advanced solid tumors. The volume of distribution (Vss) was 4,864 L (2,643 L/m² for a patient with a median BSA of 1.84 m²) at steady state.

Based on the population pharmacokinetic analysis, cabazitaxel has a plasma clearance of 48.5 L/h (CV 39%; 26.4 L/h/m² for a patient with a median BSA of 1.84 m²) in patients with metastatic prostate cancer. Following a 1-hour intravenous infusion, plasma concentrations of cabazitaxel can be described by a 3-compartment PK model with α-, β-, and γ-half-lives of 4 minutes, 2 hours, and 95 hours, respectively.

What is claimed is:

1. A method for treating a patient with prostate cancer that has progressed during or after treatment with docetaxel, comprising administering to said patient a dose of 20 to 25 mg/m² of cabazitaxel, or a hydrate or solvate thereof, in combination with a corticoid.

2. The method according to claim 1, where the prostate cancer is an advanced metastatic disease.

3. The method according to claim 1, where the cabazitaxel is in the form of an acetone solvate.

4. The method according to claim 3, in which the acetone solvate contains between 5% and 8% by weight of acetone.

5. The method according to claim 1, comprising repeating the administration of cabazitaxel, or hydrate or solvate thereof, as a new cycle every 3 weeks.

6. The method according to claim 1, wherein the cabazitaxel is in base form.

7. The method according to claim 1, wherein said cabazitaxel, or hydrate or solvate thereof, is administered in an amount to provide an AUC of about 991 ng·h/mL (CV 34%).

8. The method according to claim 1, wherein said cabazitaxel, or hydrate or solvate thereof, is administered in an amount to provide an $C_{max}$ of about 226 ng·h/mL (CV 107%).

9. The method according to claim 1 wherein said cabazitaxel, or hydrate or solvate thereof, is administered in an amount to provide a plasma clearance of 48.5 L/h (CV 39%).

10. The method according to claim 1, further comprising monitoring blood counts and measuring neutrophil levels in the patient.

11. The method according to claim 10, further comprising discontinuing cabazitaxel treatment in a patient with a neutrophil count of ≤1,500 cells/mm$^3$.

12. The method according to claim 1, where the cabazitaxel, or hydrate or solvate thereof, is administered at a dose of 25 mg/m$^2$.

13. The method according to claim 1, wherein the corticoid is selected from the group consisting of prednisone and prednisolone.

14. The method according to claim 13, where the prednisone or prednisolone is administered at a dose of 10 mg/day.

15. The method according to claim 14, where the cabazitaxel, or hydrate or solvate thereof, is administered at a dose of 20 mg/m$^2$.

16. The method according to claim 14, where the cabazitaxel, or hydrate or solvate thereof, is administered at a dose of 25 mg/m$^2$.

17. The method according to claim 1, where the prostate cancer is a castration resistant or hormone-refractory prostate cancer.

18. The method according to claim 17, where the cabazitaxel, or hydrate or solvate thereof, is administered at a dose of 25 mg/m$^2$.

19. The method according to claim 17, comprising repeating the administration of said cabazitaxel, or hydrate or solvate thereof, as a new cycle every 3 weeks.

20. The method according to claim 1, wherein the prostate cancer is a castration resistant or hormone-refractory, metastatic prostate cancer.

21. The method according to claim 20, where the cabazitaxel, or hydrate or solvate thereof, is administered at a dose of 20 mg/m$^2$.

22. The method according to claim 20, where cabazitaxel, or hydrate or solvate thereof, is administered at a dose of 25 mg/m$^2$.

23. The method according to claim 20, comprising repeating the administration of said cabazitaxel, or hydrate or solvate thereof, as a new cycle every 3 weeks.

24. The method according to claim 1, wherein the prostate cancer is a castration resistant or hormone-refractory, metastatic prostate cancer, and wherein the corticoid is selected from the group consisting of prednisone and prednisolone, and wherein the cabazitaxel, or hydrate or solvate thereof, is administered at a dose of 25 mg/m$^2$.

25. The method according to claim 24, comprising repeating the administration of said cabazitaxel, or hydrate or solvate thereof, as a new cycle every 3 weeks.

26. The method according to claim 1, where the cabazitaxel, or hydrate or solvate thereof, is administered at a dose of 20 mg/m$^2$.

27. A method of increasing the survival of a patient with a castration resistant or hormone refractory, metastatic prostate cancer that has progressed during or after treatment with docetaxel, comprising administering a dose of 20 to 25 mg/m$^2$ of cabazitaxel, or hydrate or solvate thereof, to the patient in combination with prednisone or prednisolone.

28. The method according to claim 27, where the cabazitaxel, or hydrate or solvate thereof, is administered at a dose of 25 mg/m$^2$.

29. The method according to claim 27, comprising repeating the administration of said cabazitaxel, or hydrate or solvate thereof, as a new cycle every 3 weeks.

30. The method according to claim 27, where the cabazitaxel, or hydrate or solvate thereof, is administered at a dose of 20 mg/m$^2$.

* * * * *